(12) United States Patent
Tong et al.

(10) Patent No.: US 7,501,235 B2
(45) Date of Patent: Mar. 10, 2009

(54) METHODS OF COLLECTING AND TRANSPORTING VAGINAL DISCHARGE FOR DETECTION OF INFECTIOUS ORGANISMS AND TO FACILITATE CERVICAL CANCER SCREENING

(75) Inventors: Sun-Wing Tong, 9C Carlton Building, Kowloon (HK); Olivia Wai-Hing Chan, Kowloon (HK); Tat-Chong Chow, Kowloon (HK); Vivian Yu, Kowloon (HK)

(73) Assignee: Sun-Wing Tong, Kowloon (HK)

(*) Notice: Subject to any disclaimer, the term of this patent is extended or adjusted under 35 U.S.C. 154(b) by 379 days.

(21) Appl. No.: 10/538,954

(22) PCT Filed: Dec. 24, 2003

(86) PCT No.: PCT/IB03/06203

§ 371 (c)(1),
(2), (4) Date: Jan. 19, 2006

(87) PCT Pub. No.: WO2004/059277

PCT Pub. Date: Jul. 15, 2004

(65) Prior Publication Data

US 2006/0166333 A1    Jul. 27, 2006

(51) Int. Cl.
*C12Q 1/70* (2006.01)
(52) U.S. Cl. .......................... 435/5; 73/864.91; 435/34
(58) Field of Classification Search .................. None
See application file for complete search history.

(56) References Cited

U.S. PATENT DOCUMENTS 5,571,684 A * 11/1996 Lawrence et al. ............. 435/18
6,117,090 A *  9/2000 Caillouette .................. 600/572

FOREIGN PATENT DOCUMENTS

| BE | 881711 | 5/1980 |
| EP | 0617284 A2 | 9/1994 |
| WO | WO 98/22063 | 5/1998 |
| WO | WO02/30266 A2 | 4/2002 |

OTHER PUBLICATIONS

Wright et al, "HPV DNA Testing of Self-collected Vaginal Samples Compared WIth Cytologic Screening to Detect Cervical Cancer," J. Amer. Med. Assoc., 2002, vol. 283, No. 1, pp. 81-86.*

* cited by examiner

*Primary Examiner*—Cecilia Tsang
*Assistant Examiner*—Amanda P Wood
(74) *Attorney, Agent, or Firm*—Cohen Pontani Lieberman & Pavane LLP

(57) ABSTRACT

The present invention provides a method of testing for the presence of infectious disease agents or host genetic markers comprising applying a device comprising an absorbent and porous material onto the introitus of a female patient; encouraging air drying of at least a portion of the collected vaginal discharge while the device is proximate to the introitus; and determining the presence of infectious disease agents or host genetic markers in the at least partially dried vaginal discharge.

7 Claims, 1 Drawing Sheet

Figure 1.

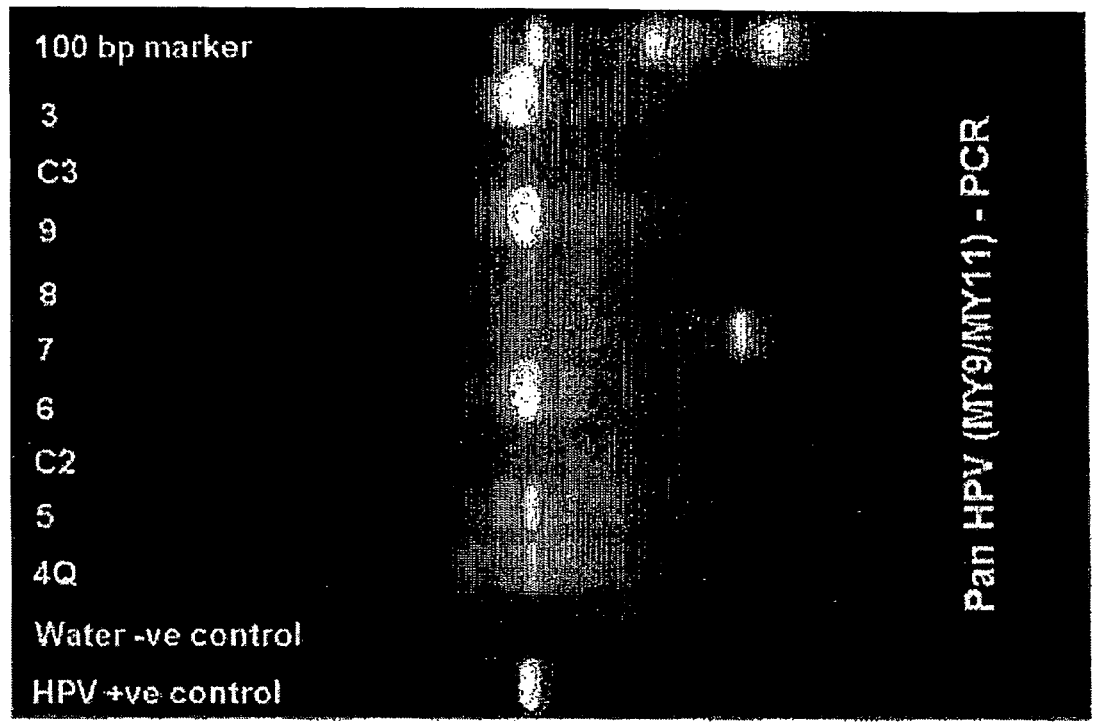

| Label (on photo) | Legend | Result |
|---|---|---|
| 100 bp marker | 100 base pair size marker | First two bands not well seen |
| 3 | Case 3 | Positive (strong) |
| C3 | Negative control 3 | Negative |
| 9 | Case 9 | Positive (strong) |
| 8 | Case 8 | Positive |
| 7 | Case 7 | Positive |
| 6 | Case 6 | Positive (strong) |
| C2 | Negative control 2 | Negative |
| 5 | Case 5 | Positive |
| 4Q* | Case 4 | Positive |
| Water -ve control | Water negative control | Negative |
| HPV +ve control | HPV positive control | Positive |

* 4Q was initially negative but became positive after using QIAamp Spin Column to purify the DNA.

METHODS OF COLLECTING AND TRANSPORTING VAGINAL DISCHARGE FOR DETECTION OF INFECTIOUS ORGANISMS AND TO FACILITATE CERVICAL CANCER SCREENING

BACKGROUND OF THE INVENTION

1. Field of the Invention

The present invention relates to methods of collection of clinical samples of biological fluids or body discharge. In particular, the invention relates to methods of collection, storage and transportation of vaginal discharge on a simple device, so as to maximize the specimen quantity and quality and to enable the detection of infectious disease agents or host genetic markers by nucleic acid amplification or other technologies.

BACKGROUND

Uterine Cervical Cancer

The cervix, or neck of the uterus, is the lower part of the uterus that opens into the upper vagina. It is also the thoroughfare for sperms entering the womb as well as being part of the birth canal. The part of the cervix exposed to the vaginal lumen is usually lined by squamous epithelium, whereas the lining of the lumen of the cervix is glandular. The junction between the two epithelia (transformation zone) is susceptible to infection by HPV (human papillomavirus). This area is also vulnerable to malignant transformation. Common cancer types in this region are squamous carcinoma and adenocarcinoma. Adenosquamous carcinoma, small cell carcinoma, lymphoma and sarcoma are rare.

Because the cervix is hidden from view, many cancers are at advanced stages when discovered, usually because they cause abnormal bleeding. Dr. George Nicolas Papanicolaou discovered in the 1920s that cells are shed from cervical cancer and when stained on glass slides, reveal themselves to the trained eyes under the microscope. That discovery ushered in early cervical cancer detection by cytological examination. As is now known, most of these cancers are caused by high-risk HPV infection (see below). Detection of HPV is now regarded as capable of giving an even earlier warning, before the cells turn obviously transformed (malignant in appearance).

The American Cancer Society estimates that 12,200 Americans will be diagnosed with cervical cancer in 2003 and up to a third will perish from it. The proportion of women who gets cervical cancer is higher in some societies, e.g. Guanacaste Province in Costa Rica.

Papanicolaou Smear (the PAP Test)

The early detection of cervical cancer has saved many lives in the 50 years since the popularization of the PAP test. The PAP test is based on microscopic interpretation of stained cervical cells that are collected onto glass slides. Through the trained eyes of cytotechnologists and cytopathologists, many early cervical neoplasia cases can be recognized before they turn into invasive cancer.

The conventional PAP test has drawbacks, owing to failure of women to obtain a PAP test, sampling error, poor specimen preparation, subjectivity inherent in any morphological interpretative tests and interpretative error. The conventional Pap smear consequently has false negative rates ranging from 13-70% and false positive of up to 14% (reference 4). The ideal screening test should have as high a sensitivity (100% sensitivity or 0% false negativity) as possible. It is clear that the Pap smear as a cancer screening test is far from being ideal (references 25 & 26). The ThinPrep® Pap Test refined the PAP test by collecting cervical cells into a liquid medium, followed by monolayer preparation on glass slide. The improvement in clarity is translated into more accurate diagnosis. However, women who fail to obtain a PAP test still cannot benefit from this form of cervical cancer screening.

Human Papillomavirus

The human body plays hosts to microorganisms, which can cause disease. Some of these enter the body through the female lower genital tract, infects the tissue and then other individuals via the same portal through sexual contact or birth.

One of these infectious disease agents is human papillomavirus (HPV). Scientific advances have elucidated the role of this virus in the causation of human cervical cancer. Over 99% of cervical cancers have detectable HPV genetic material. In particular, high risk HPV produces a host of proteins that derail the cell cycle, subvert host immune defense and perhaps take advantage of the hormonal cycle, to result in malignant transformation of cervical epithelial cells, evasion from elimination by the adaptive immune system of the host, and to enhance its transmission to other individuals.

Examples of such virus-encoded proteins include high risk HPV E7 protein, which is shown to inactivate hypophosphorylated host pRB, thereby preventing it from sequestering E2F, leading to activation of the transcription machinery by E2F and the expression of proteins that push the cell into division. In addition, E7 stimulates the S-phase genes cyclin A and cyclin E, seems to block the function of the cyclin-dependent kinase inhibitors WAF1 (p21 or CIP1) and KIP1 (p27), and amplifies the centriole, inducing aneuploidy, all of which contributing to tumorigenesis.

High risk HPVs also produce E6, which mimics cellular MDM-2, and shuttles p53 to the cytoplasmic compartment, where it is destroyed. Without p53, the guardian of the genome, malignant transformation is unchecked. Other transforming properties of E6 include destruction of the pro-apoptotic protein BAK, leading to immortalization of transformed cells, activation of telomerase and possible inhibition of degradation of SRC-family kinases.

Synergistically, E6 and E7 proteins of high-risk HPVs drive the cell into unrestrained proliferation, immortality, aneuploidy and genomic instability, necessary milestones in the malignant transformation of benign cells. Other viral factors, particularly those that subvert the adaptive immune system, interplay with host factors, such as smoking, mutagens, other infections, immunosuppression, genetic predisposition and several sexual partners, to result in clinical malignancy.

HPV Testing as an Adjunct to or in Conjunction with the Papanicolaou Smear

Since the association of HPV, in particular high-risk HPV types, with cervical cancer is established, and the molecular mechanisms of cellular transformation and viral evasion of host immune response are being understood, physicians have come to accept HPV testing as an adjunct to the PAP test or for triage of abnormal PAP tests (the Food and Drug Administration [FDA] approved the use of HPV testing in women with abnormal PAP test in March 2000).

Recently, in March 2003, the FDA approved the use of HPV detection as cervical cancer screening in conjunction with the PAP test in women older than 30 years of age (http://www.fda.gov/bbs/topics/news/2003/new00890.html).

Specimen Collection for HPV Testing

Methods of specimen collection have included biopsy, physician directed cervical scrape (similar to the process of obtaining a PAP test specimen), cervico-vaginal lavage and self-obtained specimens utilizing cervico-vaginal lavage, vaginal swab, vulval swab, self insertion and removal of vaginal tampon and urine collection.

All of these methods of obtaining clinical specimens have the serious drawback of requiring the patient to present herself to a clinic for the specimen collection, whether physician-directed or self-obtained. However, one of the major reasons why many women are still presenting with invasive cervical cancer without having a prior PAP test is the psychological barrier of denial, detest of strange environments and strangers, lack of time and other factors such as the unavailability of medical or screening facilities, particularly in developing countries. Other proposals for self-collection involve the deliberation on the part of the patient to purchase an item or to collect one from a clinic, risking stigmatization.

2. Description of the Related Art

U.S. patent application US2002/0007161 describes the use of a special collection device resembling a sanitary napkin, modified to include a removable sampling strip. Such a device although similar to the regular unmodified sanitary napkin, by virtual of its special nature, has the disadvantage that patients might feel stigmatized (psychologically) when purchasing it, because the act of purchasing or obtaining one is associated with a test for a medical condition. An example is the purchase of over-the-counter male-potency medications, if permitted by the FDA. Retaining the fluid specimen as taught in the art favors survival and continued growth and multiplication of contaminating bacteria and fungi, which produce enzymes that decompose the clinical material of interest, such as viral particles, viral nucleic acids and host genetic markers. The impermeable outer layer of the napkin while preventing soiling of the underwear and/or outside clothes presents a barrier to rapid evaporation of moisture, contributing to maintaining conditions favorable for bacterial and fungal overgrowth.

Self-obtained cervicovaginal lavage has been advocated as a means of collecting specimens for HPV testing. The method involves insertion of a device into the vagina, followed by the irrigation with a fluid and its collection. The method again involves the purchase of such a device, suffering from the same disadvantage of potential stigmatization as the above example. In addition, some patients find insertion of foreign objects into the vagina offensive.

For the same reason, patients may not like the idea of insertion of vaginal tampons as a means of collecting specimens. This and other methods involving insertion of foreign objects into the vagina are often not acceptable for virgins.

Using other devices, primarily swabs, but also tissue paper, vaginal and vulvar samples can be self-obtained by patients. However, the quantity of sample may not be sufficient for examination in some cases because it involves only a one-time collection. For the same reason, collecting urine may not give the desired sensitivity because while it washes HPV particles from the introitus into the specimen container, the quantity may not be sufficient (explaining the 72% positivity in urine as compared to the 98% positivity in paired cervical swabs; Reference 22).

Thus, a method of specimen collection that does not require the patient to attend a medical clinic, permits the largest amount of vaginal discharge to be collected, does not stigmatize the patient, and also facilitates the storage, stability, and delivery of the specimen to the laboratory for examination, is needed.

SUMMARY OF THE INVENTION

The invention provides improved methods for collection, storage and transportation of quantitatively and qualitatively superior clinical specimen from the lower female genital tract on simple devices for the purpose of testing for markers of cervical cancer, such as HPV, host genetic markers and surrogate markers such as other sexually transmitted disease(s).

Definitions

"Aneuploid" refers to not having an exact multiple of the haploid number of chromosome.

"Antibody" is a protein (immunoglobulin) that recognizes and binds to an antigen as part of the immune response.

"Antigen" means a substance with a molecular surface structure that triggers an immune response, i.e., the production of antibodies, and/or that reacts with (its) specific antibodies (antigen-antibody reaction).

"Apoptosis" refers to physiological cell death, or programmed cell death, a process that shapes an organism during development, as well as being a means to prevent viral replication or the propagation of irreparable genetic damage to progeny cells. It is an active process requiring gene transcription and the expenditure of energy.

"Cell cycle" refers to the sequence of events between mitotic divisions, conventionally divided into G0 (G for gap), G1, S (S for synthesis phase during which DNA is replicated), G2 and M (M for mitosis) phases. Cells that are not dividing are said to be in G0 phase. Cells that transited from G0 to G1 are thought to be committed to completing the cell cycle and dividing.

"Cyclins" are proteins expressed during the cell cycle. Their levels vary markedly during different phases of the cell cycle, unlike their corresponding partner, the cyclin-dependent kinases, which levels do not fluctuate during the cell cycle. The complexes are activated by phosphorylation, and the active kinase then phosphorylates a variety of proteins involved in mitosis, DNA replication, depolymerization of the nuclear lamina, and mitotic spindle formation.

"Cyclin-dependent kinases (CDKs)" are enzymes that are only active when they form a complex with cyclins.

"Cyclin-dependent kinase inhibitors" include two families of proteins, the so-called INK4 inhibitors, comprising p16, p15, p18 and p19, which act on cyclin D/CDK4 and cyclin D/CDK6, and the second group, comprising p21, p27 and p57, which inhibit all CDKs.

"Hybridization" means fusion of two single complementary DNA strands (DNA/DNA hybridization), or the fusion of complementary DNA and RNA strands (DNA/RNA hybridization).

"LOH (loss of heterozygosity)" refers to the loss of an allele. When LOH occurs, inactivation of the remaining allele by mutational inactivation results in complete loss of function of the corresponding gene. If the gene product is a tumor suppressor, then tumorigenesis is not inhibited.

"MDM-2" refers to an oncoprotein that inhibits p53 by binding to the transcriptional activator domain of p53, preventing if from regulating its target. MDM-2 expression is activated by p53 and promotes degradation of p53 by the proteasome.

"Microsatellite" refers to small run (usually less than 0.1 kb) of tandem repeats of a very simple DNA sequence, usually 1-4 bp, for example $(CA)_n$.

"Microsatellite instability" refers to a phenomenon characteristic of certain tumor cells, where during DNA replication the repeat copy number of microsatellites is subject to random changes.

"p53" is a tumor suppressor gene product, whose function is protean, and include the arrest of the cell cycle in the event of DNA damage and the induction of apoptosis if the DNA damage cannot be repaired. Because of its central role in preventing tumors, it is found to be inactivated in a little over 50% of human tumors.

"Polymerase chain reaction (PCR)" refers to a technique for making many copies of a stretch of DNA sequence in the test tube. It employs repetitive thermal cycling consisting of denaturation of double-stranded DNA, annealing of appropriate oligonucleotide primers, and extension of the primer by polymerase enzyme.

"Polymorphism" means the existence of two or more variants (alleles, phenotypes, sequence variants, chromosomal structure variants) at significant frequencies in the population.

"Proto-oncogene (cellular oncogene)" refers to a eukaryotic gene that regulates cell growth or division and when present in truncated form in a retrovirus, behaves as an oncogene, capable of malignant transformation of a eukaryotic cell after integration into the cell genome.

"Reverse transcriptase" refers to an enzyme complex that occurs in RNA viruses and that can synthesize DNA from an RNA template.

"Reverse-transcription PCR (RT-PCR)" refers to the technique for amplification of RNA involving first the synthesis of DNA complementary (cDNA) to a stretch of target RNA employing the enzyme reverse transcriptase, followed by PCR of the cDNA.

"Single nucleotide polymorphisms (SNPs)" refers to common DNA sequence variations among individuals.

"Telomerase" refers to a ribonucleoprotein enzyme that adds nucleotide bases at the telomere.

BRIEF DESCRIPTION OF THE DRAWINGS

FIG. 1 is a photograph of a slab of agarose gel with DNA amplification products separated by electrophoresis, showing the presence of bands specific for HPV in samples of air-dried vaginal discharge and positive control and absence of bands in negative controls.

The agarose gel is stained with ethidium bromide to highlight the amplified DNA under UV-light. The DNA is size fractionated by electrophoresis and shows distinct bands at the predicted location (450 bps), as compared with the 100 bps DNA size ladder at the top (the 100 & 200 bps bands did not show very well in this photograph). Because amplification only occurs with a given set of primers (in this case MY09/11) when HPV is present, the presence of a sharp band at 450 bps is indicative of the presence of HPV in the specimen. Negative controls (clinical samples and water) are negative. Positive control is positive.

DETAILED DESCRIPTION OF THE PRESENTLY PREFERRED EMBODIMENTS

According to the invention, the entire process of specimen collection is performed by the patient in the privacy of her own home using self-purchased disposable underwear of any kind of fabrication, preferably absorbent and porous. Alternatively, regular underwear, pantyhose, or a one-time imprint or swab with clean toilet paper are acceptable. Regular clothing is accepted with the understanding that it will be used as a clinical sample and not returnable to the patient.

The soft fabric of the underwear or alternative, herein known as device, moulds onto the anatomical contours of the introitus, facilitating the transfer of even small amounts of vaginal discharge from the introitus to the absorbent material of the device. A comparatively stiff sanitary napkin may only absorb more copious discharge that drains onto the napkin. If discharge is small in volume, it will preferentially stick to the skin of the introitus rather than adhering to the fabrics of the napkin.

Bacterial and fungal contamination of the underwear or sanitary napkin is inevitable because they may already be present in the vaginal discharge, and skin, and because of the proximity of the introitus to the anus.

Because the fabric of the device is thin and porous, water in the vaginal discharge readily penetrates from the inner surface to the outer surface and escapes into the environment. This natural drying process is facilitated if a skirt, instead of an outside pants is worn. Air-drying thus achieved, is instrumental to the success of the invention, because air-drying of the vaginal discharge stops enzymatic activity of bacteria and host polymorphonuclear neutrophils from breaking down viral particles, viral nucleic acid, host genetic markers and other materials of interest, by the process of decomposition. Air-drying of the vaginal discharge also prevents bacterial and fungal overgrowth.

Addition of anti-bacterial and anti-fungal agents to the device becomes unnecessary. In addition, these additives may be allergenic, inhibitory or complicating subsequent laboratory investigations, or are otherwise unacceptable.

This invention however, does not exclude the use of these additives as an adjunct or prevents the use of special fabric that is inherently inhibitory to bacterial or fungal overgrowth, such as by extracting moisture, thus rendering the secretions dry, or by providing a hostile environment for the growth of microorganisms, yet in no way harming the patient, causing allergic reactions, or compromising subsequent laboratory examination of the specimen.

In the morning, the device is worn as if a normal underwear for any period of time, usually until it is changed later in the day. The patient is advised to wear a skirt instead of pants, and not to wear additional undergarment(s) on top of the underwear. At the end of the period, the patient removes the device and puts it into a self-purchased, previously unused, zip-lock plastic bag.

Before or after insertion into the bag, the device if still moist, is dried briefly for about one minute by the gentle cool draft of a consumer-type electric hair drier.

After gently expressing excess air, the zip-lock bag is sealed, without decontamination, addition of preservative, desiccant or additional processing.

Next the specimen (device containing vaginal discharge) is inserted into a regular envelope and mailed to the laboratory together with return address (unique identifier but not name, and email, address, and/or telephone number) at the earliest convenience.

The patient provides a unique "name" or "identifier" that identifies the specimen, so that reporting can be made anonymously by post, newspaper, poster, the Internet, or other means. The identifying information should not be the patient's real name but must be unique and known only to the patient.

To prevent intentional, ill-willed, grafting of the results on another person, common names are not accepted. Such specimens may be destroyed without testing.

On the other hand, specimens that originate from patients who attend medical clinics are allowed to be associated with the real names and contact information of the patients, so that results can be discreetly communicated to them through the health agency.

In the laboratory, the incoming specimens are opened, registered and tested.

Initial Preparation of the Specimen for DNA Extraction Consists of the Following Steps:

1. Individually opening the specimen bags in an appropriate biosafety cabinet using decontaminated instruments.
2. Visual identification of the area of the specimen that contains visible stains, which is usually at the most dependent part of the underwear.
3. Cutting or punching out a full-thickness piece of the stained specimen measuring from 0.2×0.2 cm to 1×1 cm.
4. Insertion of the procured specimen into an Eppendorf tube followed by DNA extraction.
5. Optional measurement of the DNA content by spectrometry after extraction, to determine if dilution is required before subsequent amplification.
6. Dilution, if required of the extracted DNA.

For HPV Testing, the Extracted DNA is Processed in the Following Way:

1. Amplification of HPV DNA from the extracted DNA by the PCR reaction or another method of nucleic acid amplification, using any number of separate reactions employing any number of primer pairs, or in one reaction using a multiplex of primer pairs.
2. Identification of the amplification product by size fractionation using gel electrophoresis or hybridization (microarray, macroarray, dot blots, line blots, reverse line blots, or antibody-based detection), so as to detect and type the HPV strain(s), if present.

Investigation of Host Genetic Material:

For studying markers of malignant or premalignant transformation of cellular DNA, the DNA is extracted as mentioned above. The DNA is then subjected to analysis, which include but is not limited to, hypermethylation of promoter sequences of p16 or other tumor suppressors, microsatellite alterations (LOH or instability), amplification of proto-oncogenes, suppression, mutational inactivation or LOH (loss of heterozygosity) of tumor suppressor genes, SNP (single nucleotide polymorphism), such as p53 gene polymorphism, or alteration of the pattern of gene expression.

Investigation of Host Gene Expression:

For the purpose of analysis of over-expression of certain mRNA species, such as p16INK4a (encoded by CDKN2A), MCMs (mini-chromosome maintenance) or TERT (catalytic subunit of telomerase), which is over-expressed in most cervical intraepithelial neoplasias, the specimens are extracted for mRNA, which is then reversely transcribed into cDNA and subsequently or simultaneously quantified using a quantitative method of nucleic acid amplification.

Investigation of Surrogate Markers for Cervical Cancer:

For the purpose of detecting surrogate markers of cervical neoplasia, the extracted DNA can be analyzed by nucleic acid technology for sexually transmitted infections, such as Chlamydia trachomatis, Neiserria gonorrhea, Treponema pallidum, Adenoassociated virus, Trichomonas vaginalis, etc.

EXAMPLES

1. Detection of HPV in vaginal discharge.

We were able to detect HPV in air-dried vaginal discharge from 45 samples (100%) obtained from women with histological confirmation of cervical HPV infection or cervical neoplasia.

We extracted DNA from the specimens using the following protocol:

1. Add 600 ul Cell Lysis Solution and 3 ul Proteinase K (20 mg/ml). Vortex to mix and incubate at 56° C. overnight.
2. Cool sample to room temperature (RT). Remove the specimen using a sterile long 10 ul pipette tip fitted to an autopipette and expel all lysate by pressing it against the inside of the tube.
3. Add 200 ul Protein Precipitation Solution to the cell lysate. Vortex vigorously at high speed for 20 sec. to mix.
4. Centrifuge at 14,000 rpm for 5 min. The precipitated proteins will form a tight pellet. If the protein pellet is not tight, repeat the centrifugation.
5. Pipette the supernatant containing the DNA (leaving behind the precipitated protein pellet, which is discarded) into a clean 1.5 ml microfuge tube containing 600 ul 100% isopropanol. Add 1.0 ul glycogen solution (20 mg/ml, a DNA carrier).
6. Mix the sample by inverting gently 50 times.
7. Centrifuge at 14,000 rpm for 2 min. A white DNA pellet may or may not be visible, depending on the yields. If the DNA yield is expected to be low (<1 ug), increase the centrifugation time to 5 min.
8. Pipette off supernatant as far as possible, a 10 ul pipette is required for final pipetting.
9. Add 300 ul 70% ethanol and invert tube several times to wash the DNA pellet.
10. Centrifuge at 14,000 rpm for 5 min, carefully pipette off supernatant as far as possible, a 10 ul pipette is required for final pipetting. Pellet may be loose, so pipette slowly and watch pellet. With the cap open, air dry the pellet at room temperature for 15 min.
11. Add 30 ul DNA Hydration Solution.

From the extracted DNA, we performed PCR in two separate tubes per specimen, employing different primer pairs:

Primer sequences:

```
Primers GP5+/6+ (reference 23):
PCR primer-GP5+ (5' to 3')
TTTGTTACTGTGGTAGATACTAC
PCR primer-GP6+ (5' to 3')
CTTATACTAAATGTCAAATAAAAAG Primers MY09/11* (reference 24):
PCR primer-MY09 (5' to 3')  CGTCCMAARGGAWACTGATC
(forward)
PCR primer-MY11 (5' to 3')  GCMCAGGGWCATAAYAATGG
(reverse)
*Degenerate sequence of the target specific capture
probe and hemiprobes shown in lower case letters.
The following represent the possible nucleic acids
incorporated:
r = A or G;
y = C or T;
m = A or C;
k = G or T;
w = A or T (A, adenosine; C, cytosine; G, gua-
nosine; T, thymidine).
```

Reaction 1. Primer pair GP5+/6+:

| Master mix reagents | Volume (ul) |
| --- | --- |
| 10× Buffer | 2.5 |
| MgCl2 (25 mM) | 3.5 |
| Primer GP5+ (10 pmol/ul) | 2.5 |
| Primer GP6+ (10 pmol/ul) | 2.5 |
| DNTPs (10 mM each) | 0.5 |
| Taq (5 U/ul) | 0.1 |
| DW | 8.4 |
| Sub-total: | 20 |
| DNA | 5 |
| Total: | 25 |

PCR Conditions:

Primer pair HPV GP5+/6+:

| Hot start: | 94° C. | 4 mins | |
| --- | --- | --- | --- |
| Denaturation: | 94° C. | 1 min | |
| Annealing: | 40° C. | 2 mins | ×40 cycles |
| Extension: | 72° C. | 1 min 30 sec | |
| Final extension: | 72° C. | 4 mins | |
| Incubation: | 4° C. | until gel electrophoresis | |

Expected size on gel electrophoresis: 140-150 bps.

Reaction 2. Primer pair MY09/11:

| Master mix reagents | Volume (ul) |
| --- | --- |
| 10× Buffer | 2.5 |
| MgCl2 (25 mM) | 2.5 |
| Primer MY09 (10 pmol/ul) | 1.25 |
| Primer MY11 (10 pmol/ul) | 1.25 |
| DNTPs (10 mM each) | 0.1 |
| Taq (5 U/ul) | 0.1 |
| DW | 12.3 |
| Sub-total: | 20 |
| DNA | 5 |
| Total: | 25 |

PCR Conditions:

Primer pair HPV MY09/11:

| Hot start: | 94° C. | 5 mins | |
| --- | --- | --- | --- |
| Denaturation: | 94° C. | 1 min | |
| Annealing : | 55° C. | 1 min 30 sec | ×40 cycles |
| Extension: | 72° C. | 1 min | |
| Final extension: | 72° C. | 5 mins | |
| Incubation: | 4° C. | until gel electrophoresis | |

Expected size on gel electrophoresis: 450 bps.

After amplification, we perform agarose gel electrophoresis for size fractionation of the PCR product. A representative gel image is shown in FIG. 1.

Early result of our experiments was reported in a peer-reviewed journal (reference 5).

Reference 5 discloses the successful detection of human papillomavirus on sanitary napkins. The present invention improves on the disclosed detection method by providing, instead of a regular napkin, a device to collect the vaginal discharge that promotes the air drying of the vaginal discharge while the device is proximate to the introitus. As discussed above, drying of the vaginal discharge reduces or stops enzymatic activity of bacteria and host polymorphonuclear neutrophils from breaking down viral particles, viral nucleic acid, host genetic markers and other materials of interest, by the process of decomposition. Air-drying of the vaginal discharge also prevents bacterial and fungal overgrowth.

The following is excerpted from Reference 5 to show the successful detection of HPV from vaginal discharge samples.

Human papillomavirus was successfully detected by polymerase chain reaction (PCR) in menstrual blood or vaginal discharge collected in sanitary napkins in 100% of 17 women having koilocytosis, cervical intraepithelial neoplasia, or squamous carcinoma.

We advocate this form of cervical cancer screening because of its high sensitivity and acceptance by patients. Diagn. Cytopathol. 2003; 28:140-141. © 2003 Wiley-Liss, Inc.

Testing for cervical human papillomavirus (HPV) infection is being investigated as a means of cervical cancer screening.

1Some investigators have tested for HPV on vaginal tampons2 and have shown high patient acceptance3 and concordance with physician-directed swab4.

We tested the hypothesis of diagnosing genital HPV infection based on the PCR of menstrual blood or vaginal discharge collected on sanitary napkins. We recruited a total of 10 patients, 7 with a pathological diagnosis of HPV infection, 2 with grade 1 cervical intraepithelial neoplasia, and 1 with invasive squamous carcinoma of the cervix.

Soiled intermenstrual or sanitary napkins containing menstrual blood were air-dried by a blower, placed in ziplock plastic bags, and sent to us by regular mail. Small pieces of the napkins were cut out (1 cm×1 cm×1 mm) using sterile scissors for direct DNA extraction. We used the same amplification protocol5 for both types of specimens, employing consensus primers GP5+ and GP6+ (biopsies and napkins) and, in a different set of reactions (napkins only), primers MY09' and MY11. Gel electrophoresis was performed after 40 cycles of amplification. HPV was detected in the sanitary napkins in 100% (10/10) of cases. Nine specimens were positive using primer set GP5+/6+. One specimen (case 4) negative with GP5+/6+ tested positive with MY09/11.

Although the number of cases was small, the 100% sensitivity is encouraging. Significantly, even a minimally soiled napkin (case 9) contained sufficient HPV DNA for detection. This study supported the hypothesis that HPV DNA remains detectable in vaginal discharge collected on sanitary napkins up to 7 weeks later and despite contamination by blood.

In populations where the prevalence of HPV infection and/or the rate of Pap testing are low, women can be targeted for Pap test or colposcopy by first testing for HPV status on soiled sanitary napkins. While a negative test is not a complete reassurance, a positive HPV test justifies the trouble, embarrassment, and time of the woman for a Pap test. Patients may even choose to be anonymous when testing for HPV. In this way, more patients may be screened by at least one of the two methods. Adoption of this paradigm shift may extend cervical cancer screening to a larger population of women.

Note Added in Proof

Seven additional specimens of intermenstrual soiled napkins were tested with 100% positivity.

REFERENCES

1. Schiffman M, Herrero R, Hildesheim A. HPV DNA testing in cervical cancer screening: results from women in a high-risk province of Costa Rica. JAMA 2000;283:87-93.
2. Harper D M, Hildesheim A, Cobb J L, Greenberg M, Vaught J, Lorincz A T. Collection devices for human papillomavirus. J Fam Pract 1999; 48:531-535.
3. Fairley C K, Chen S, Tabrizi S N, Quinn M A, McNeil J J, Garland S M. Tampons: a novel patient-administered method for the assessment of genital human papillomavirus infection. J Infect Dis 1992;165:1103-1106.
4. Harper D M, Noll W W, Belloni D R, Cole B F. Randomized clinical trial of PCR-determined human papillomavirus detection methods: self-sampling versus clinician-directed biologic concordance and women's preferences. Am J Obstet Gynecol 2002;186:365-373.
5. Zehbe I, Wilander E. Two consensus primer systems and nested polymerase chain reaction for human papillomavirus detection in cervical biopsies: a study of sensitivity. Hum Pathol 1996;27:812-815.

REFERENCES

1. Cannistra S A, Niloff J M. Cancer of the uterine cervix. N Engl J Med. 1996 Apr. 18;334(16):1030-8.
2. Walboomers J M, Jacobs M V, Manos M M, Bosch F X, Kummer J A, Shah K V, Snijders P J, Peto J, Meijer C J, Munoz N. Human papillomavirus is a necessary cause of invasive cervical cancer worldwide. J Pathol. 1999 September;189(1):12-9.
3. Sawaya G F, Brown A D, Washington A E, Garber A M. Clinical practice. Current approaches to cervical-cancer screening. N Engl J Med. 2001 May 24;344(21):1603-7.
4. Baldwin P, Laskey R, Coleman N. Translational approaches to improving cervical screening. Nat Rev Cancer. 2003 March;3(3):217-26.
5. zur Hausen H. Papillomaviruses and cancer: from basic studies to clinical application. Nat Rev Cancer. 2002 May;2(5):342-50.
6. Tindle R W. Immune evasion in human papillomavirus-associated cervical cancer. Nat Rev Cancer. 2002 January;2(1):59-65.
7. Tong T R, Chan O W, Chow T C, Yu V, Leung K M, To S H. Detection of human papillomavirus in sanitary napkins: a new paradigm in cervical cancer screening. Diagn Cytopathol. 2003 March;28(3):140-1.
8. Human Papillomaviruses: Natural History and Virology. http://www.fda.gov/ohrms/dockets/ac/01/slides/3805S1_02%20Unger/index.htm.
9. Nobbenhuis M A, Helmerhorst T J, van den Brule A J, Rozendaal L, Jaspars L H, Voorhorst F J, Verheijen R H, Meijer C J. Primary screening for high risk HPV by home obtained cervicovaginal lavage is an alternative screening tool for unscreened women. J Clin Pathol. 2002 June;55(6):435-9.
10. Harper D M, Noll W W, Belloni D R, Cole B F. Randomized clinical trial of PCR-determined human papillomavirus detection methods: self-sampling versus clinician-directed—biologic concordance and women's preferences. Am J Obstet Gynecol. 2002 March;186(3):365-73.
11. Fairley C K, Chen S, Tabrizi S N, Quinn M A, McNeil J J, Garland S M. Tampons: a novel patient-administered method for the assessment of genital human papillomavirus infection. J Infect Dis. 1992 June;165(6):1103-6.
12. Wright T C Jr, Denny L, Kuhn L, Pollack A, Lorincz A. HPV DNA testing of self-collected vaginal samples compared with cytologic screening to detect cervical cancer. JAMA. 2000 Jan. 5;283(1):81-6.
13. Sellors J W, Lorincz A T, Mahony J B, Mielzynska I, Lytwyn A, Roth P, Howard M, Chong S, Daya D, Chapman W, Chernesky M. Comparison of self-collected vaginal, vulvar and urine samples with physician-collected cervical samples for human papillomavirus testing to detect high-grade squamous intraepithelial lesions. CMAJ. 2000 Sep. 5;163(5):513-8.
14. Gray R H, Wawer M J, Girdner J, Sewankambo N K, Serwadda D, Meehan M, Gaydos C, Li C, Quinn T. Use of self-collected vaginal swabs for detection of Chlamydia trachomatis infection. Sex Transm Dis. 1998 September;25(8):450.
15. Kailash U, Hedau S, Gopalkrishna V, Katiyar S, Das B C. A simple 'paper smear' method for dry collection, transport and storage of cervical cytological specimens for rapid screening of HPV infection by PCR. J Med Microbiol. 2002 July;51(7):606-10.
16. Klaes R, Benner A, Friedrich T, Ridder R, Herrington S, Jenkins D, Kurman R J, Schmidt D, Stoler M, von Knebel Doeberitz M. p16INK4a immunohistochemistry improves interobserver agreement in the diagnosis of cervical intraepithelial neoplasia. Am J Surg Pathol. 2002 November;26(11):1389-99.
17. Negri G, Egarter-Vigl E, Kasal A, Romano F, Haitel A, Mian C. p16INK4a is a useful marker for the diagnosis of adenocarcinoma of the cervix uteri and its precursors: an immunohistochemical study with immunocytochemical correlations. Am J Surg Pathol. 2003 February;27(2):187-93.
18. zur Hausen H. Papillomavirus and p53. Nature. 1998 May 21;393(6682):217.
19. Storey A, Thomas M, Kalita A, Harwood C, Gardiol D, Mantovani F, Breuer J, Leigh I M, Matlashewski G, Banks L. Role of a p53 polymorphism in the development of human papillomavirus-associated cancer. Nature. 1998 May 21;393(6682):229-34.
20. Dong S M, Kim H S, Rha S H, Sidransky D. Promoter hypermethylation of multiple genes in carcinoma of the uterine cervix. Clin Cancer Res. 2001 July;7(7):1982-6.
21. Nuovo G J, Plaia T W, Belinsky S A, Baylin S B, Herman J G. In situ detection of the hypermethylation-induced inactivation of the p16 gene as an early event in oncogenesis. Proc Natl Acad Sci USA. 1999 Oct. 26;96(22):12754-9.
22. Stanczuk G A, Kay P, Allan B, Chirara M, Tswana S A, Bergstrom S, Sibanda E N, Williamson A L. Detection of human papillomavirus in urine and cervical swabs from patients with invasive cervical cancer. J Med Virol. 2003 September;71(1):110-4.
23. M V Jacobs, A M de Roda Husman, A J van den Brule, P J Snijders, C J Meijer and J M Walboomers. Group—specific differentiation between high- and low-risk human papillomavirus genotypes by general primer—mediated PCR and two cocktails of oligonucleotide probes. J Clin Microbiol. 1995 April;33(4):901-5.
24. Yarkin F, Chauvin S, Konomi N, Wang W, Mo R, Bauchman G, Diaz A, Burstein D, Szporn A, Hauptman E, Zhang D Y. Detection of HPV DNA in cervical specimens collected in cytologic solution by ligation-dependent PCR. Acta Cytol. 2003 May-June;47(3):450-6.
25. Franco E L. Are we ready for a paradigm change in cervical cancer screening? Lancet. 2003 Dec. 6;362(9399):1866-7.
26. Cuzick J, Szarewski A, Cubie H, Hulman G, Kitchener H, Luesley D, McGoogan E, Menon U, Terry G, Edwards R, Brooks C, Desai M, Gie C, Ho L, Jacobs I, Pickles C, Sasieni P. Management of women who test positive for high-risk types of human papillomavirus: the HART study. Lancet. 2003 Dec. 6;362(9399):1871-6.

The invention claimed is:

1. A method of testing for the presence of human papillomavirus or host genetic markers comprising: applying a device comprising an absorbent and porous material onto the introitus of a female patient to collect vaginal discharge, either briefly as an imprint or swab, or over a period of time; encouraging air drying of the collected vaginal discharge; and determining the presence of human papillomavirus or host genetic markers in the air-dried vaginal discharge.

2. The method of claim 1 wherein the device is a regular or disposable underwear.

3. The method of claim 1 further comprising the step of storing the dried vaginal discharge in a container, without added desiccants, preservatives or other additives.

4. The method of claim 1 wherein the steps of determining the presence of human papillomavirus comprises nucleic acid amplification and specific identification of the amplified product(s).

5. The method of claim 1 wherein the host genetic markers are of malignant or pre-malignant transformation of cellular DNA.

6. The method of claim 1 wherein the host genetic markers are of cellular mRNA.

7. The method of claim 6 where the mRNA is selectively amplified, identified and quantified.

* * * * *